US012642547B2

(12) United States Patent
Rebar et al.

(10) Patent No.: US 12,642,547 B2
(45) Date of Patent: Jun. 2, 2026

(54) DEVICE, SYSTEM AND METHOD FOR TREATMENT OF HEMORRHOIDS

(71) Applicant: BOSTON SCIENTIFIC SCIMED, INC., Maple Grove, MN (US)

(72) Inventors: Hannah Rebar, Brighton, MA (US); Nathan Thomas Cummings, Worcester, MA (US); Nora Belkhayat, Framingham, MA (US); Jan Weber, Maastricht (NL); Jessica Powers, Brookline, MA (US); Collin Murray, Bolton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 133 days.

(21) Appl. No.: 18/784,376

(22) Filed: Jul. 25, 2024

(65) Prior Publication Data

US 2024/0374274 A1 Nov. 14, 2024

Related U.S. Application Data

(63) Continuation of application No. 16/912,124, filed on Jun. 25, 2020, now Pat. No. 12,070,237.

(Continued)

(51) Int. Cl.
*A61B 17/221* (2006.01)
*A61B 1/31* (2006.01)
*A61B 17/00* (2006.01)

(52) U.S. Cl.
CPC .............. *A61B 17/221* (2013.01); *A61B 1/31* (2013.01); *A61B 2017/00407* (2013.01); *A61B 2017/2212* (2013.01)

(58) Field of Classification Search
CPC ............ A61B 17/12009; A61B 17/221; A61B 17/32056; A61B 2017/00407; A61B 2017/0474; A61B 2017/0477; A61B 2017/12018; A61B 2017/2212; A61B 1/31; A61B 2017/1225; A61B 17/122;
(Continued)

(56) References Cited

U.S. PATENT DOCUMENTS 5,281,238 A * 1/1994 Chin ................ A61B 17/12013
606/139
6,610,072 B1 * 8/2003 Christy .............. A61B 17/0483
606/144

(Continued)

*Primary Examiner* — Kankindi Rwego
(74) *Attorney, Agent, or Firm* — Fay Kaplun & Marcin, LLP

(57) ABSTRACT

A device for treating hemorrhoids includes a first ligating member which moves between a first position in which the first member is tightened to a degree required to maintain a desired position of the first member around the first portion without significantly cutting off blood flow and a second configuration in which the first member is cinched down around the first portion to substantially cut off blood flow to the encircled first portion. Also, the device includes a first applicator having a proximal lumen and first and second opposed distal lumens open to the proximal lumen. The first member is extending from a proximal end distally through the proximal lumen into the first lumen to exit a distal end of the first lumen, loop around and enter the distal end of the second lumen. The first member is passing through the second lumen into the proximal lumen.

16 Claims, 9 Drawing Sheets

Related U.S. Application Data

(60)  Provisional application No. 62/874,640, filed on Jul. 16, 2019.

(58)  Field of Classification Search
      CPC ............ A61B 17/1222; A61B 17/1227; A61B 17/128; A61B 2017/00353; A61B 2017/00358; A61B 2017/2215; A61B 2017/2217; A61B 2017/3452; A61B 8/06; A61F 6/20; A61F 6/202; A61F 6/204; A61F 6/206; A61F 6/208; A01K 1/06
      USPC ................................. 600/104; 606/127, 140
      See application file for complete search history.

(56)                References Cited

U.S. PATENT DOCUMENTS

| | | | |
|---|---|---|---|
| 2011/0106107 A1* | 5/2011 | Binmoeller ...... | A61B 17/12013 606/139 |
| 2016/0051278 A1* | 2/2016 | Jacobs ............. | A61B 17/32056 606/113 |

* cited by examiner

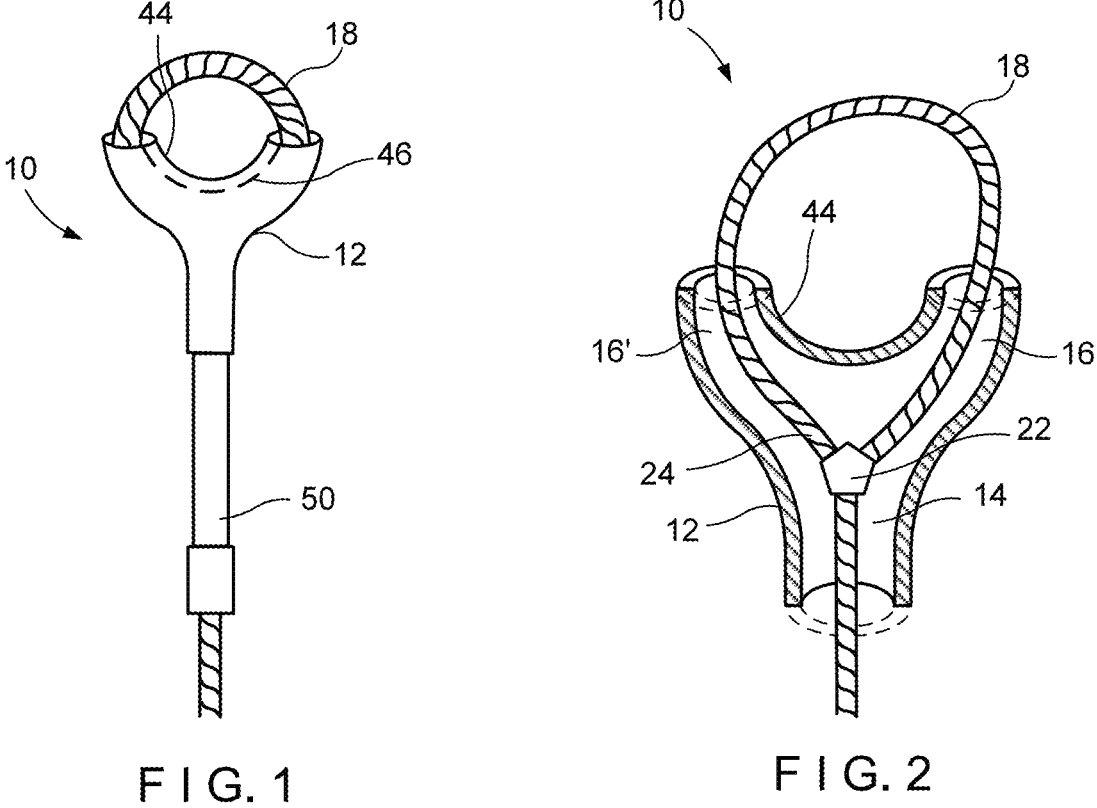
F I G. 1          F I G. 2
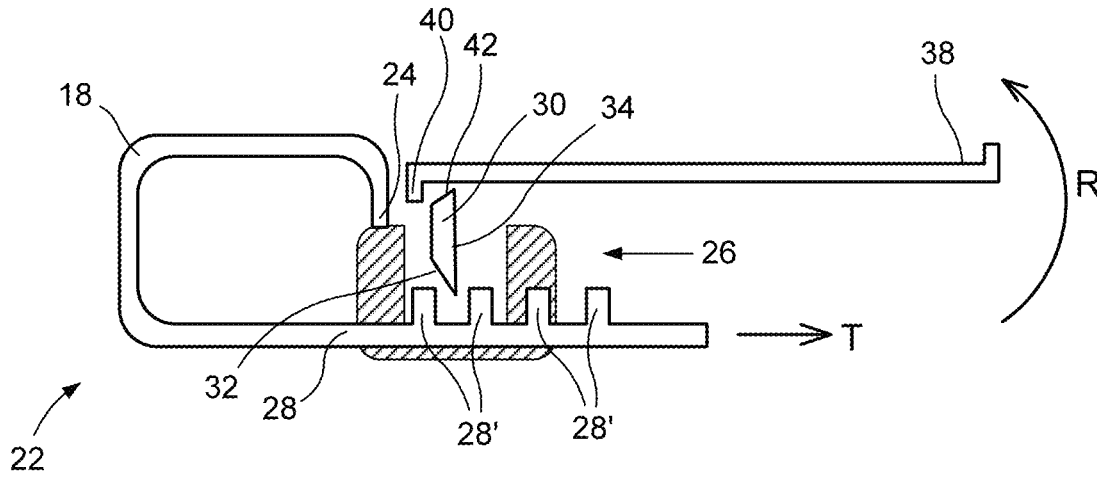
F I G. 3A

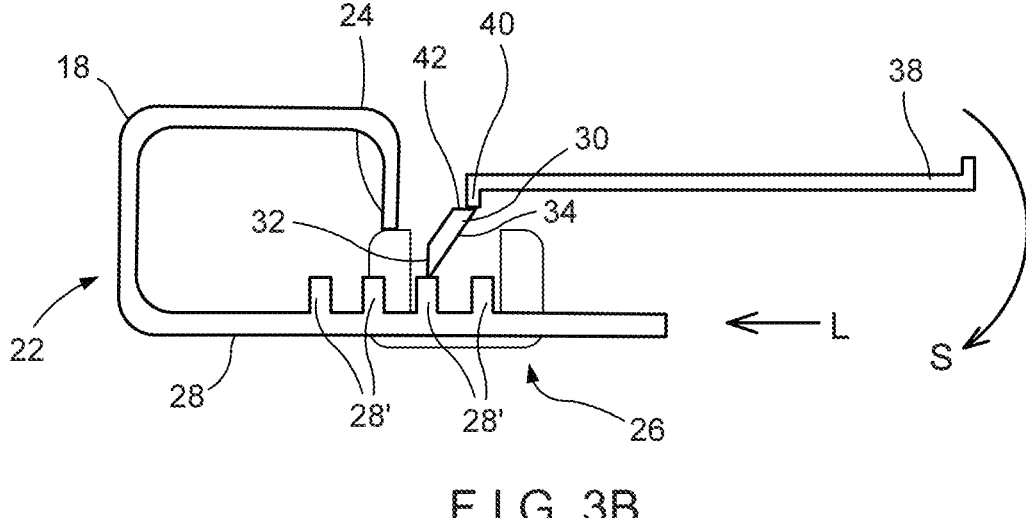
F I G. 3B
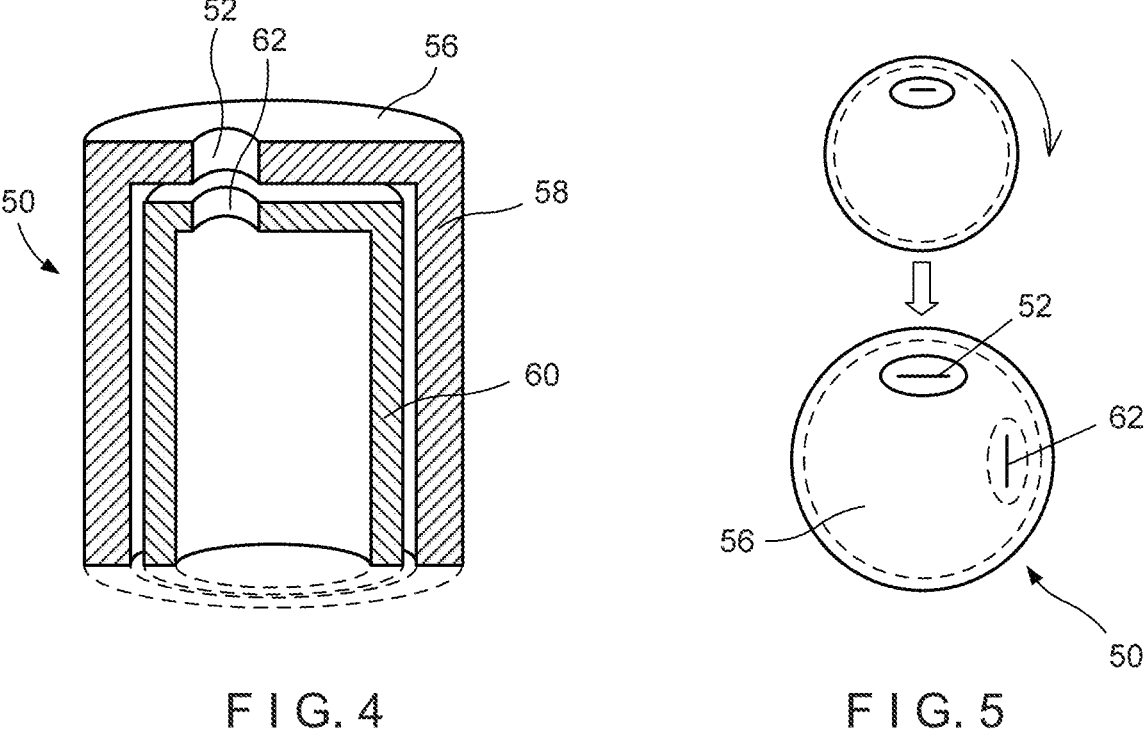
F I G. 4
F I G. 5

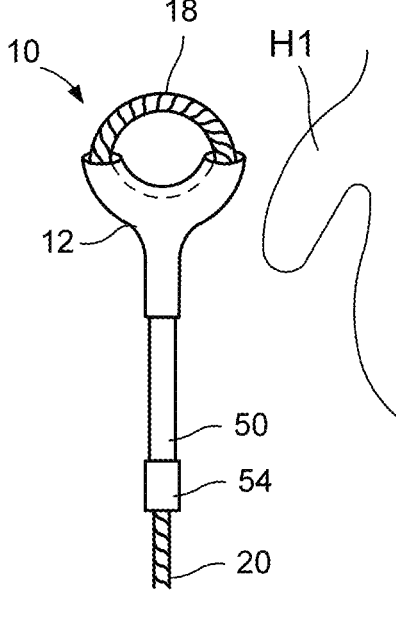
F I G. 6
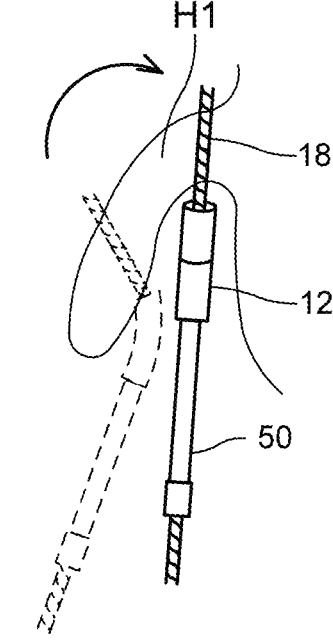
F I G. 7
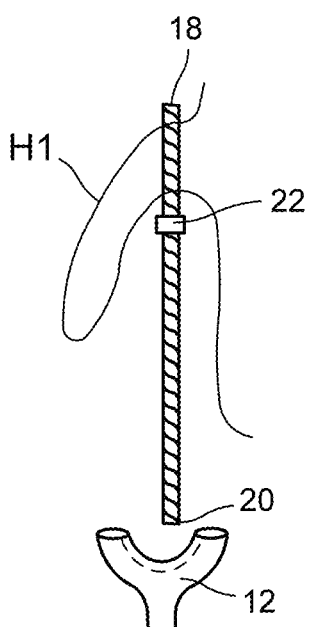
F I G. 8
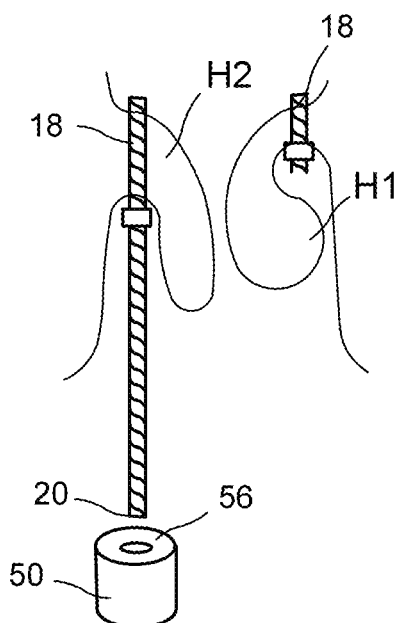
F I G. 9

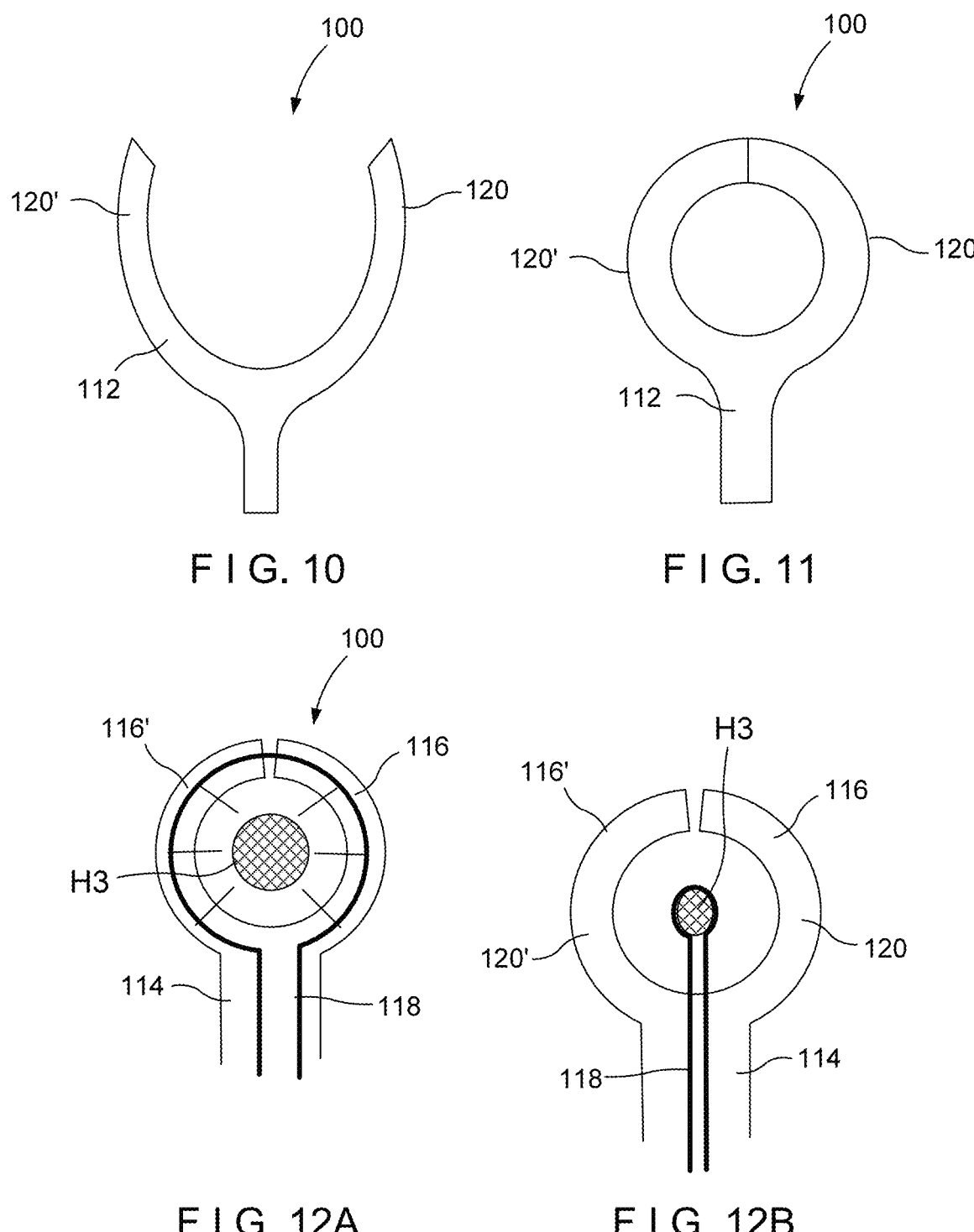
F I G. 10
F I G. 11
F I G. 12A
F I G. 12B

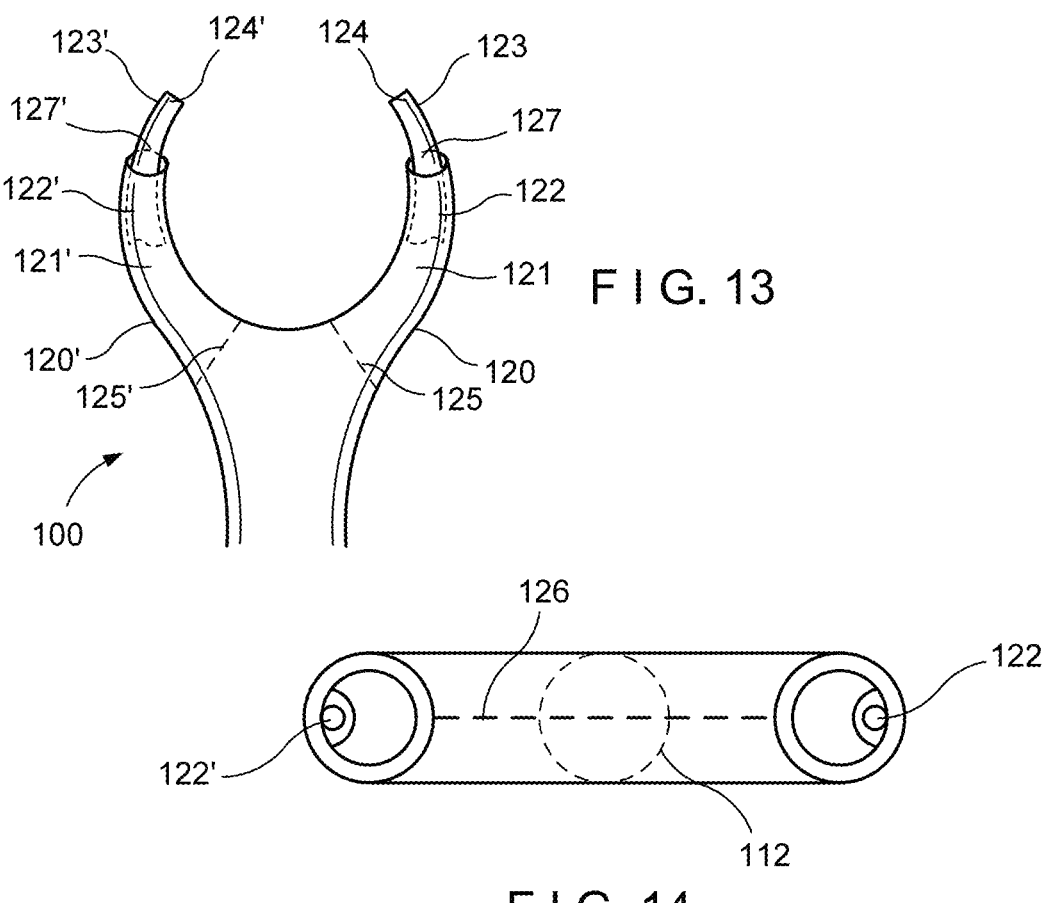
F I G. 13
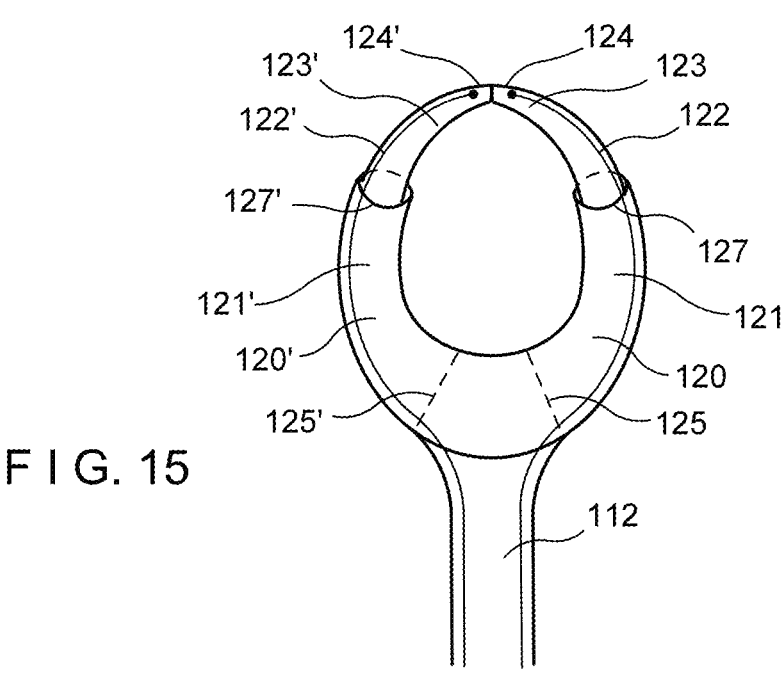
F I G. 14
F I G. 15

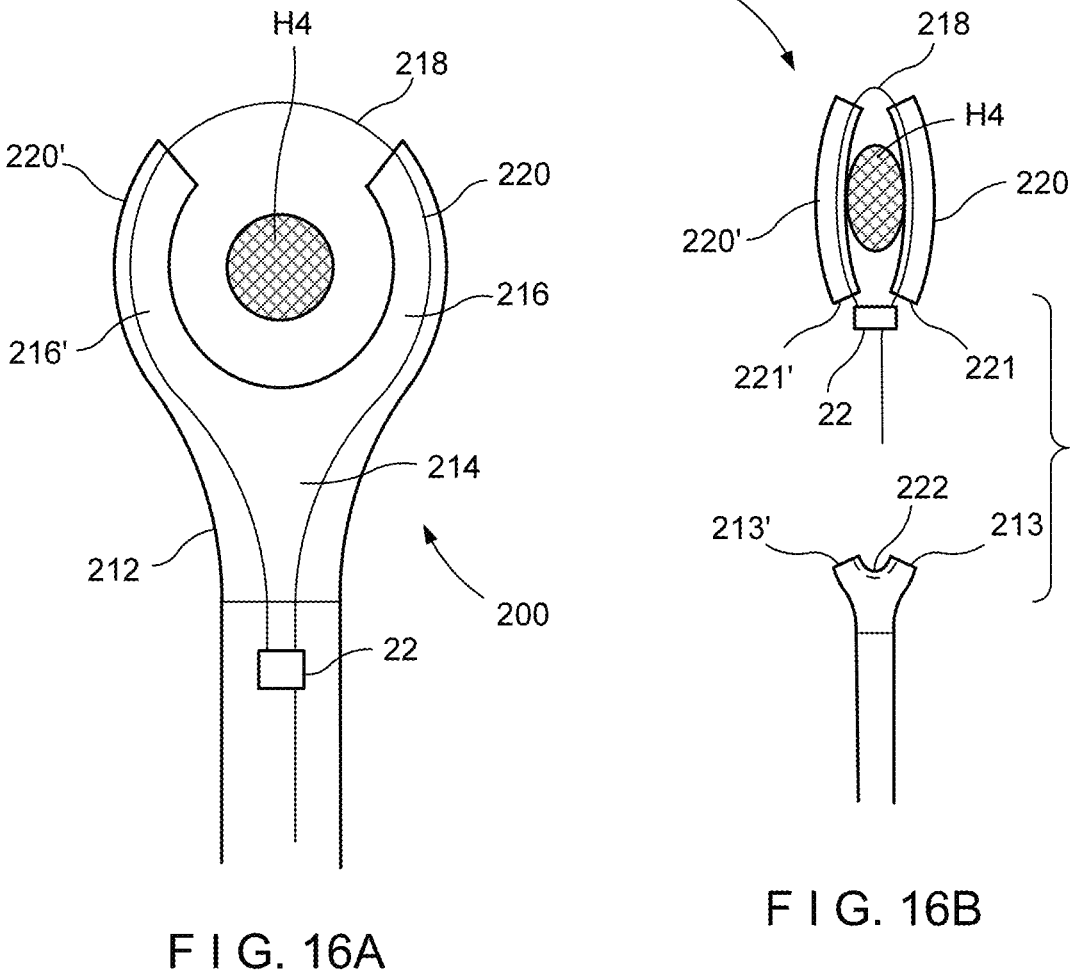
F I G. 16A
F I G. 16B
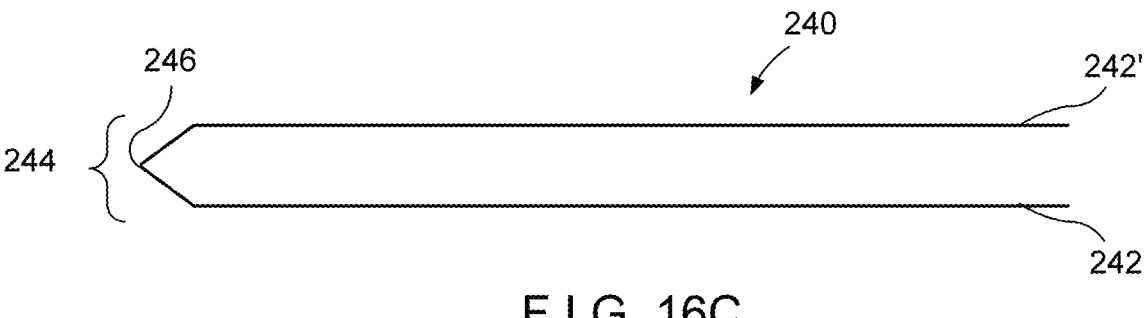
F I G. 16C

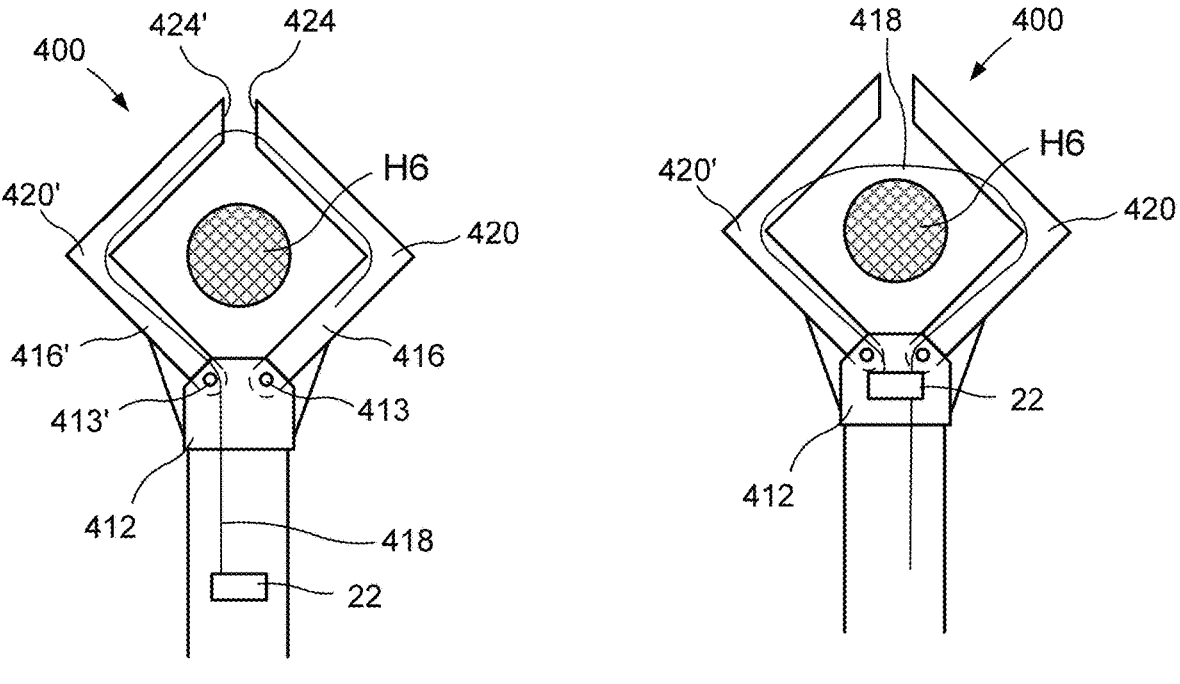
F I G. 20A
F I G. 20B
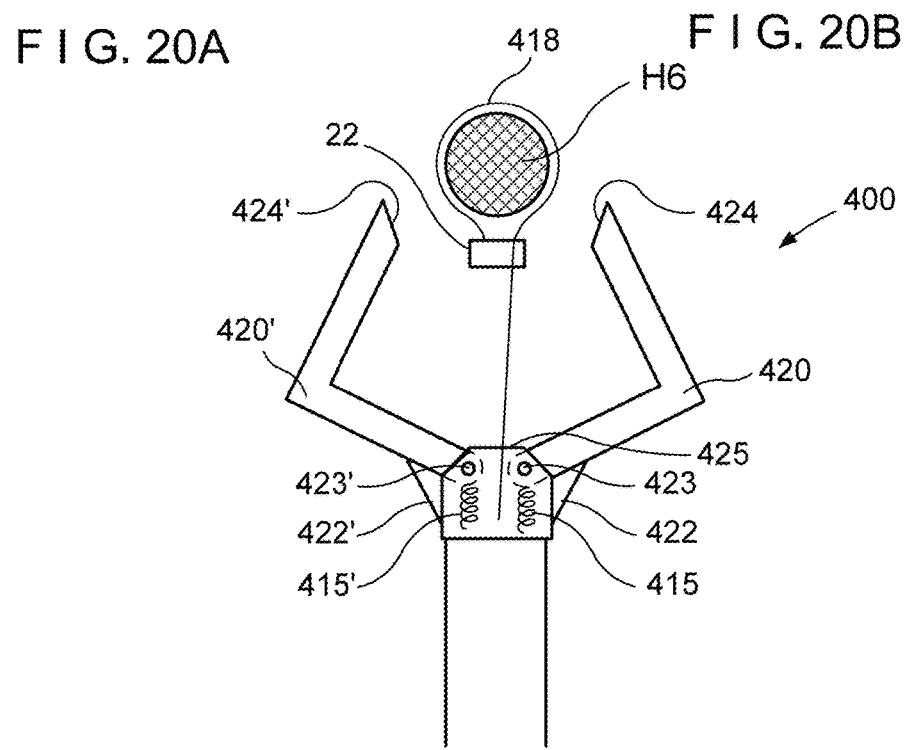
F I G. 20C

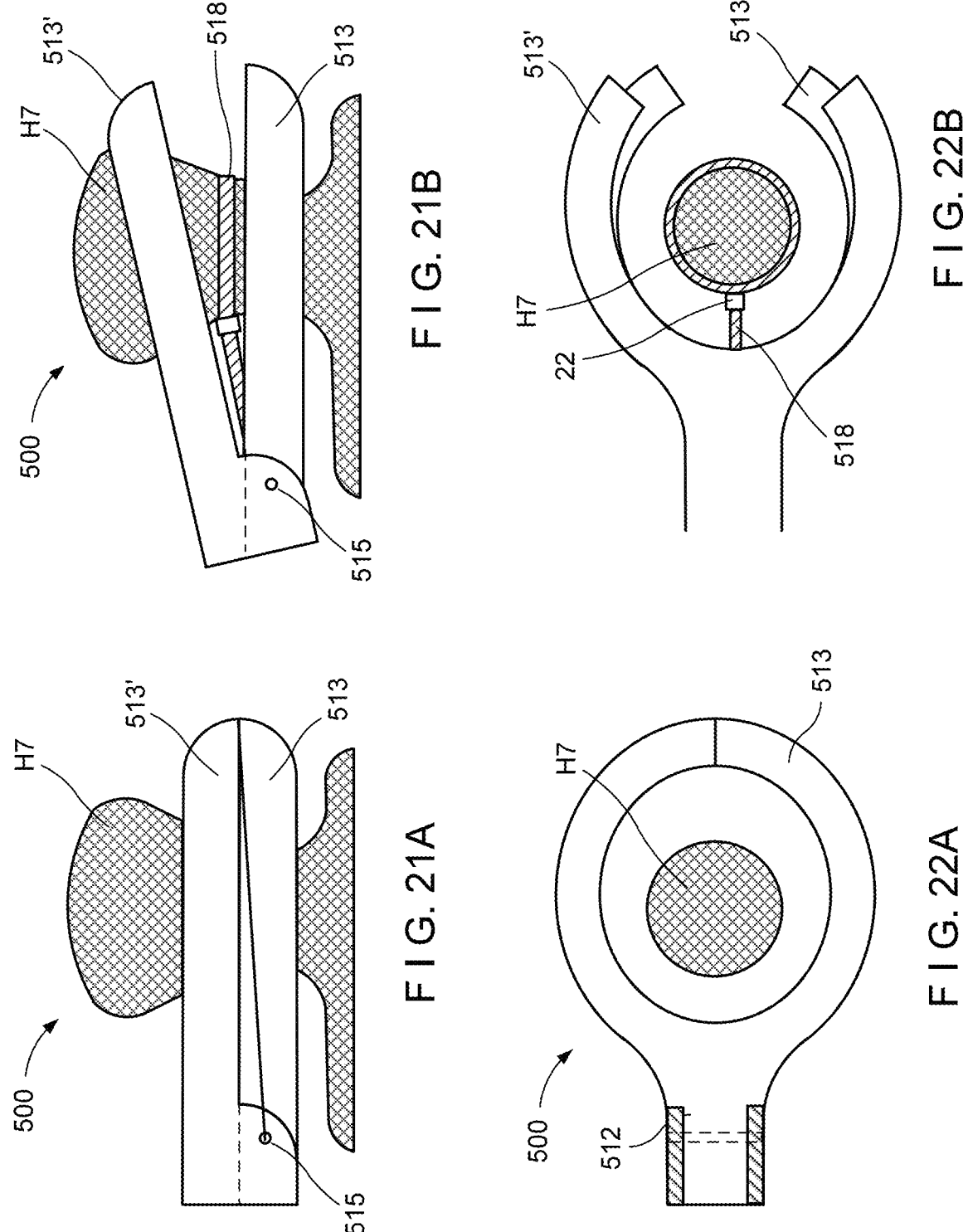
F I G. 21B
F I G. 22B
F I G. 21A
F I G. 22A

DEVICE, SYSTEM AND METHOD FOR TREATMENT OF HEMORRHOIDS

PRIORITY CLAIM

The present application is a Continuation of U.S. patent application Ser. No. 16/912,124 filed Jun. 25, 2020, which claims priority to U.S. Provisional Patent Application Ser. No. 62/874,640 filed Jul. 16, 2019. The disclosures of the above application(s)/patent(s) are incorporated herewith by reference.

FIELD

The present disclosure relates generally to devices, systems and methods for treating hemorrhoids and, more specifically, for treating multiple hemorrhoids during a single procedure.

BACKGROUND

Hemorrhoids are swollen and inflamed veins around the anus or in the lower rectum. Hemorrhoids may be external, forming under the skin around the anus, or internal, forming in the lining of the anus and the lower rectum.

The treatment of hemorrhoids by ligation can often be difficult as the earlier ligated hemorrhoids often swell to the point that this interferes with the treatment of remaining hemorrhoids, making visualization and/or access to remaining hemorrhoids difficult.

SUMMARY

The present disclosure relates to a device for treating hemorrhoids comprising a first ligating member configured to encircle and cut off blood flow to a first portion of target tissue, the first ligating member structured to move from a first position maintaining configuration in which the first ligating member is tightened to a degree required to maintain a desired position of the first ligating member around the first portion of target tissue without significantly cutting off blood flow to the first portion of target tissue and a second configuration in which the first ligating member is cinched down around the first portion of target tissue to substantially cut off blood flow to the encircled first portion of target tissue and a first applicator including a proximal lumen and first and second opposed distal lumens open to the proximal lumen, the first ligating member extending from a proximal end distally through the proximal lumen of the first applicator into the first distal lumen of the first applicator to exit a distal end of the first distal lumen of the first applicator, loop around and enter the distal end of the second distal lumen of the first applicator, the first ligating member passing through the second distal lumen of the first applicator into the proximal lumen of the first applicator.

In an embodiment, the device further includes a first hub through which a proximal portion of the first ligating member passes from the proximal lumen of the first applicator to the first distal lumen of the first applicator, a distal portion of the first ligating member re-entering the first hub to pass from the second distal lumen of the first applicator to the proximal lumen of the first applicator.

In an embodiment, the first hub and the first ligating member are configured so that the first hub locks the first ligating member in a desired position to maintain a desired compression on tissue received between the first applicator and a portion of the first ligating member extending between the distal ends of the first and second lumens of the first applicator.

In an embodiment, the first applicator includes a slit on a distal surface thereof through which the first ligating member may pass after the first ligating member has been placed around a first target portion of tissue so that the first applicator may be withdrawn from the body while leaving the first ligating member in place around the first portion of target tissue.

In an embodiment, the first hub is movable from a first configuration in which a loop of the first ligating member extending from the first hub through the first distal lumen of the first applicator and back through the second distal lumen of the first applicator to the first hub can only be tightened and a second configuration in which the loop of the first ligating member can be loosened and tightened.

In an embodiment, the first hub includes a first ratchet mechanism and a first actuation switch which, when moved from a first position in which an engagement member of the first ratchet mechanism prevents a loosening of the loop of the first ligating member to a second position that moves the engagement member of the first ratchet mechanism out of engagement with the first ligating member to permit the first ligating member to move through the first hub in tightening and loosening directions.

In an embodiment, the first applicator is formed as a substantially Y shaped housing with the first and second lumens thereof extending through first and second branches, respectively, the first and second branches of the first applicator being biased toward a tissue capture configuration in which the distal ends of the first and second lumens of the first applicator are open to one another.

In an embodiment, the device further includes first and second pull wires coupled to the first and second branches of the first applicator, respectively, so that, when the first and second pull wires are drawn proximally through the first applicator, the first and second branches of the first applicator are drawn away from each other to move from the tissue capture configuration to a tissue receiving configuration.

In an embodiment, the first ligating member is pre-loaded in the first applicator so that target tissue is passed through a center of a loop of the ligating member to position the first ligating member around the target tissue.

In an embodiment, the first applicator is configured to be advanced to a position adjacent to the target tissue when the first and second branches of the first applicator have been drawn apart into the tissue receiving configuration, the first applicator being configured then to revert to the tissue capture configuration after the target tissue has been positioned between the first and second branches thereof so that the first ligating member may be threaded through the proximal lumen of the first applicator and the first distal lumen into the second distal lumen of the first applicator and back into the proximal lumen of the first applicator to pass around the target portion of tissue.

In an embodiment, The device further includes a first hub through which a proximal portion of the first ligating member passes from the proximal lumen of the first applicator to the first distal lumen of the first applicator, a distal portion of the first ligating member re-entering the first hub to pass from the second distal lumen of the first applicator to the proximal lumen of the first applicator, wherein the first hub and the first ligating member are configured so that the first hub locks the first ligating member in a desired position to maintain a desired compression on tissue received between the first applicator and a portion of the first ligating member extending between the distal ends of the first and second lumens of the first applicator.

The present disclosure also relates to a system for treating hemorrhoids which includes an insertion device including a working channel and a visualization system; a first ligating member configured to encircle and cut off blood flow to a first portion of target tissue, the first ligating member structured to move from a first position maintaining configuration in which the first ligating member is tightened to a degree required to maintain a desired position of the first ligating member around the first portion of target tissue without significantly cutting off blood flow to the first portion of target tissue and a second configuration in which the first ligating member is cinched down around the first portion of target tissue to substantially cut off blood flow to the encircled first portion of target tissue; and a first applicator including a proximal lumen and first and second opposed distal lumens open to the proximal lumen, the first ligating member extending from a proximal end distally through the proximal lumen of the first applicator into the first distal lumen of the first applicator to exit a distal end of the first distal lumen of the first applicator, loop around and enter the distal end of the second distal lumen of the first applicator, the first ligating member passing through the second distal lumen of the first applicator into the proximal lumen of the first applicator, the first ligating member and the first applicator being sized and shaped for insertion through a working channel of the insertion device to the first portion of target tissue.

In an embodiment, the system further includes a first hub through which a proximal portion of the first ligating member passes from the proximal lumen of the first applicator to the first distal lumen of the first applicator, a distal portion of the first ligating member re-entering the first hub to pass from the second distal lumen of the first applicator to the proximal lumen of the first applicator.

In an embodiment, the first hub and the first ligating member are configured so that the first hub locks the first ligating member in a desired position to maintain a desired compression on tissue received between the first applicator and a portion of the first ligating member extending between the distal ends of the first and second lumens of the first applicator.

In an embodiment, the first applicator includes a slit on a distal surface thereof through which the first ligating member may pass after the first ligating member has been placed around a first target portion of tissue so that the first applicator may be withdrawn from the body while leaving the first ligating member in place around the first portion of target tissue.

Furthermore, the present disclosure relates to a method for ligating tissue which includes tightening a first ligating member about a first portion of target tissue to an initial level of tissue compression sufficient to maintain a desired position of the first ligating member around the first portion of target tissue without significantly cutting off blood flow to the first portion of target tissue; tightening a second ligating member about a second portion of target tissue to the initial level of tissue compression; and after the second ligating member has been tightened to the initial level of tissue compression, tightening the first ligating member about the first portion of target tissue to a final level of tissue compression sufficient to cut off blood flow to the first portion of target tissue and tightening the second ligating member about the second portion of target tissue to the final level of tissue compression.

In an embodiment, a trimming device contains an outer housing with a sharpened outer opening and an inner housing rotatably received therein with a sharpened inner opening, the method further comprising, aligning the outer opening and inner opening, inserting a proximal portion of the first ligating member through the outer opening and inner opening, rotating the outer housing relative to the inner housing to remove the proximal portion from the first ligating member, and after removing the proximal portion of the first ligating member, re-aligning the outer opening with the inner opening, inserting a proximal portion of the second ligating member through the outer opening and inner opening, and rotating the outer housing relative to the inner housing to remove the proximal portion from the second ligating member.

In an embodiment, the method further includes tightening to the initial level the first ligating member around the first portion of target tissue by drawing a proximal portion of the first ligating member through a hub within a first applicator, the first ligating member passing into a proximal lumen of the first applicator through the hub and into a first distal lumen of the first applicator, looping out of a distal end of the first distal lumen of the first applicator and entering a distal end of a second distal lumen of the first applicator, wherein a user places the first portion of target tissue within a loop of the first ligating member extending between the distal ends of the first and second distal lumens of the first applicator.

In an embodiment, the method further includes after tightening the first ligation member to the initial level, tightening to the initial level the second ligating member around the second portion of target tissue by drawing a proximal portion of the second ligating member through the hub within the first applicator, the second ligating member passing into the proximal lumen of the first applicator through the hub and into the first distal lumen of the first applicator, looping out of the distal end of the first distal lumen of the first applicator and entering the distal end of the second distal lumen of the first applicator, wherein the user places the second portion of target tissue within the loop of the second ligating member extending between the distal ends of the first and second distal lumens of the first applicator.

In an embodiment, the method further includes after tightening the first and second ligation members to the initial level, tightening the first ligating member about the first portion of target tissue to the final level and tightening the second ligating member about the second portion of target tissue to the final level.

BRIEF DESCRIPTION

FIG. 1 shows a perspective view of a device for treating hemorrhoids according to a first exemplary embodiment;

FIG. 2 shows a cut-away view of a distal end of the device of FIG. 1;

FIG. 3A shows a cut-away view of a hub of the device of FIG. 1 in a first configuration;

FIG. 3B shows a cut-away view of the hub of FIG. 3A in a second configuration;

FIG. 4 shows a cut-away view of the trim tool of the device of FIG. 1;

FIG. 5 shows an end view of the trim tool of FIG. 4;

FIG. 6 shows a perspective view of the device of FIG. 1 adjacent to a first hemorrhoid to be treated; and

5

Figures 17, 18, 19:
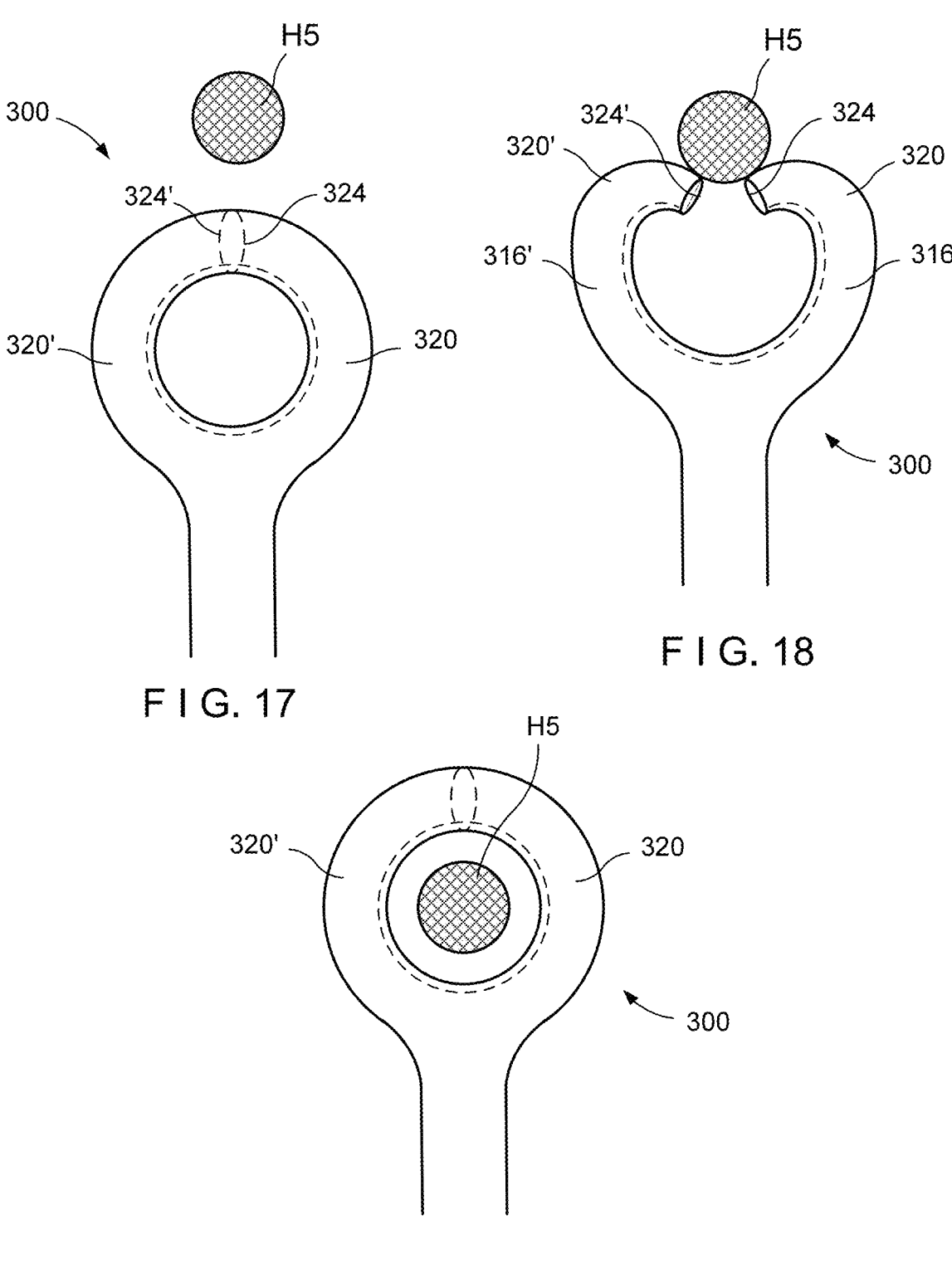

FIG. 7 shows the device of FIG. 1 in first and second positions for a preliminary step in ligating hemorrhoids according to an exemplary method;

FIG. 8 shows the device of FIG. 1 with a first ligation band preliminarily positioned around a first hemorrhoid to be treated according to the exemplary method FIG. 9 shows the device of FIG. 1 with the first ligation band in a final position around the first hemorrhoid to be treated and a second ligation band in a preliminary position around a second hemorrhoid to be treated;

FIG. 10 shows a device for treating hemorrhoids according to a second embodiment in a tissue receiving configuration;

FIG. 11 shows the device of FIG. 10 in a tissue capture configuration;

FIG. 12A shows a partially cross-sectional view of the device of FIG. 10 in the tissue capture configuration around a target portion of tissue;

FIG. 12B shows a partially cross-sectional view of the device of a FIG. 10 after a ligation band has been partially deployed therefrom;

FIG. 13 shows a partially cross-sectional view of a device of FIG. 10 in a tissue receiving configuration;

FIG. 14 shows an end view of the device of FIG. 13 in the tissue capture configuration;

FIG. 15 shows a perspective view of the device of FIG. 13 in a tissue capture configuration;

FIG. 16A shows a partially cross-sectional view of the device of a third embodiment in tissue capture configuration around a target portion of tissue;

FIG. 16B shows a partially cross-sectional view of the device of FIG. 16A in a collapsed state;

FIG. 16C shows a banding agent for use in conjunction with the device of FIG. 16A;

FIG. 17 shows a device according to a fourth embodiment in an initial configuration;

FIG. 18 shows the device of FIG. 17 in an intermediate configuration abutting a target portion of tissue;

FIG. 19 shows the device of FIG. 17 in a tissue capture configuration;

FIG. 20A shows a partially cross-sectional view of a device according to a fifth embodiment in a tissue capture configuration with a ligation band fed therethrough around a target portion of tissue;

FIG. 20B shows a partially cross-sectional view of the device of FIG. 20A with the ligation band partially removed from the device;

FIG. 20C shows the device of FIG. 20A in an open configuration with the ligation band removed therefrom;

FIG. 21A shows a side view of a device according to a sixth embodiment in a tissue capture configuration;

FIG. 21B shows a side view of the device of FIG. 21A in an open configuration;

FIG. 22A shows a top view of the device of FIG. 21A in the capture configuration; and FIG. 22B shows a top view of the device of FIG. 21A in the open configuration.

DETAILED DESCRIPTION

The present disclosure may be further understood with reference to the following description and the appended drawings, wherein like elements are referred to with the same reference numerals. The present disclosure is directed to a device and method for treating multiple hemorrhoids in a single procedure. It is noted that the terms Aproximal@ and Adistal,@ as used herein, refer to a direction toward (proximal) and away from (distal) a user of the device. Although the embodiments described herein a specifically configured for the treatment of internal hemorrhoids, those skilled in the art will understand that the embodiments described herein may also be employed to treat similar lesions and polyps (benign, cancerous, etc.) that are close enough to the rectum such that they could be reached with such a device.

Although embodiments of the present disclosure are described herein with respect to hemorrhoid treatment, it is understood that the device may be for any tissue treatment procedure, for ligating and removing a selected tissue. For example, another similar application is closing the Left Atrial Appendix (LAA) from an external site of the heart, whereby a small incision is made between the ribs allowing a laparoscope with such a band-clamping device to close of part of the LAA.

As shown in FIGS. 1 and 9, a device 10 for treating hemorrhoids includes a generally Y shaped housing 12 including a single proximal lumen 14 that branches into two distal lumens 16, 16' extending distally from the lumen 14. A ligation band 18 extends from a proximal end 20 into the lumen 14 to a hub 22. The ligation band 18 extends through the hub 22 to pass out of the lumen 16 to loop around and enter the lumen 16'. The ligation band 18 passes through the lumen 16' to re-enter the hub 22 to which a distal end 24 of the ligation band 18 is immovably coupled. The ligation band 18 may be substantially inelastic (i.e., does not need to be stretchable). However, the ligation band 18 may be formed of a material having any desired level of elasticity.

As shown in FIGS. 3A and 3B, the hub 22 includes a ratchet mechanism 26 that engages a corrugated surface 28 of the ligation band 18 so that the ligation band 18 can be drawn into the hub 22 to tighten the ligation band around target tissue (e.g., hemorrhoid H1) but the ligation band 18 is locked to prevent inadvertent loosening. In some embodiments, as shown in FIGS. 3A and 3B, a ratchet mechanism 26 is movable between a first configuration in which the ligation band 18 is locked against movement through the hub 22 to loosen the loop extending between the lumens 16, 16' (i.e., moved through the hub 22 in the direction of the arrow L in FIG. 3B) but permitted to be drawn through the hub 22 to tighten the loop between the lumens 16, 16' (i.e., moved through the hub 22 in the direction of arrow T in FIG. 3A) and a second configuration in which the ratchet mechanism 26 is disengaged to permit the ligation band 18 to move through the hub 22 in either direction. This permits a user to loosen and remove a ligation band 18 that, for example, has not been positioned as desired over the hemorrhoid H1.

The ligation band 18 may then be re-positioned as desired until the desired positioning has been achieved. However, those skilled in the art will understand that the ratchet mechanism 26 may be constructed to remain permanently in the first configuration in which the loop in the ligation band 18 can be tightened but not loosened. In this case, each ligation band 18 could not be loosened for removal from tissue over which it has been tightened. In such an embodiment, the construction of the ratchet mechanism 26 would be substantially similar as will be described below except that components for moving the ratchet mechanism 26 between the first and second configurations would not be present.

The ratchet mechanism 26 includes an engagement member 30 which, in the first configuration, protrudes toward the corrugations on the surface 28 of the ligation band 18. The engagement member 30 includes a first ramped surface 32 facing the portion of the ligation band 18 extending from the hub 22 toward the distal end 24 of the ligation band 18 while the proximal surface 34 of the engagement member 30 (facing the proximal end 20 of the ligation band 18) is not ramped. The engagement member 30 is rotatably coupled to a housing of the hub 22 and is configured so that, in a resting state, the engagement member 30 protrudes between the corrugations 28' of the surface 28 and is structured so that, in the first configuration) it may rotate away from this resting position (shown in FIG. 3A) only in the direction of the arrow R (FIG. 3A) as the first ramped surface 32 engages the corrugations 28' moving in the direction of the arrow T. If, in the first configuration, a distally directed force is applied to the ligation band 18 (i.e., in a direction opposite the arrow T), the proximal surface 34 of the engagement member 30 will engage the distal surface of one of the corrugations 28' and prevent the ligation band 18 from moving through the hub 22 in this direction. Those skilled in the art will understand that the operation of the hub 22 in the first configuration is substantially the same as would be the operation of a hub 22 that is structured to be permanently in the first configuration.

The hub 22 of this embodiment, however, includes an actuation switch 38 that moves the engagement member 30 away from the rest position shown in FIG. 3A by rotating the engagement member 30 in the direction of arrow S (FIG. 3B) until the engagement member 30 extends out of engagement with the corrugations 28' permitting the ligation band 18 to move through the hub 22 in either the direction T or L. Specifically, the actuation switch 38 of this embodiment includes an abutment 40 adjacent to a second ramped surface 42 at an end of the engagement member 30 opposite the first ramped surface 32 (i.e., an end opposite the end of the engagement member 30 that engages the corrugations 28').

In the first configuration (FIG. 3A), the abutment 40 is positioned distally of the second ramped surface 42 permitting the engagement member 30 to remain in the rest position (except when engaged by the corrugations 28') so that it protrudes between the corrugations 28'. To move the ratchet mechanism 26 from the first to the second configuration, the actuation switch 38 of this embodiment is drawn proximally so that the abutment 40 engages the second ramped surface 42 as shown in FIG. 3B to rotate the engagement member 30 in the direction of arrow S until the engagement member 30 is moved out of engagement with the corrugations 28'. Those skilled in the art will understand that the actuation switch 38 may be coupled to an actuator on a handle of an applicator via, for example, a pull wire.

In addition, as would be understood by those skilled in the art, other mechanisms may be substituted for the ratchet mechanism 26 and the actuation switch 38 so long as, these mechanisms operate, in a first configuration, to permit movement of the ligation band 18 through the hub 22 in only one direction and, in a second configuration, to permit movement of the ligation band 18 through the hub 22 in both directions. As would be understood by those skilled in the art, the devices 10 may be provided by a manufacturer with the ligation band 18 pre-loaded within the housing 12 and the hub 22 with the ligation band 18 in loose state ready to receive tissue within the distal loop.

The housing 12 according to this embodiment includes at a distal end 44 thereof, extending from the lumen 16 to the lumen 16', a slit 46 which, when the ligation band 18 has been tightened around target tissue as desired, the housing 12 may be pulled open to release the ligation band 18 and the hub 22 from the housing 12. Specifically, after the ligation band 18 has been fully tightened around target tissue as will be described in more detail below, the housing 12 may be pulled proximally so that the loop of the ligation band 18 is pulled distally out of the housing 12 via the slit 46. The ligation band 18 may be dimensioned, for example, so that the proximal end 20 remains outside the body accessible to the user of the device 10 even when the device 10 is implanted over target tissue as desired.

A system for implanting the devices 10 may also include a trim tool 50 as shown in FIGS. 1, 4-6, 7 and 9. The trim tool 50 may be used, as will be described below, to aid in advancing the device(s) 10 through, for example, an anoscope to the desired locations within the body and placing the device(s) 10 on target tissue (e.g., hemorrhoids H1 and H2). As will be discussed in more detail below, a first device 10 is preliminarily positioned over a target portion of tissue (e.g., hemorrhoid H1) and tightened only enough to hold the first device 10 in the desired position. The degree of tightening at this stage is less than that required to ligate tissue as this reduces the swelling that would result if the tissue were fully ligated.

The user may preliminarily tighten the ligation band 18 of any of the devices 10 by grasping the proximal end 20 of the ligation band 18 and pulling proximally while pushing distally on the trim tool 50 through which the proximal portion of the ligation band 18 extends. The trim tool 50 abuts the proximal end of the housing 12 so that, as the ligation band 18 is drawn proximally through the hub 22, the loop of the ligation band 18 extending between the lumens 16, 16' is tightened around the target tissue received through the loop until the ligation band 18 is tightened sufficiently around the hemorrhoid.

For example, a user may be able to determine sufficient tightness of the ligation band 18 by direct visualization of the hemorrhoid through the anoscope or by a tactile change in the force required to pull the proximal end 20 of the ligation band 18. The user would experience increased resistance, indicating that the ligation band 18 is tightening around the hemorrhoid. The housing 12, according to this embodiment, has an inner diameter/outer diameter (ID/OD) interface fit, snap-on feature, or similar that allows it to be selectively connected or disconnected to the trim tool 50 by the user. Thus, the user withdraws the trim tool 50 from the proximal portion of the ligation band 18 and pulls the housing 12 proximally to remove the housing 12 from the ligation band 18 by having the ligation band 18 pass through the slit 46 of the housing 12.

The user then repeats this process to place additional devices 10 on additional target portions of tissue (e.g., hemorrhoid H2) which might otherwise be impeded by the intense swelling that often results when ligating devices are fully tightened around target tissue. That is, the lack of swelling of the hemorrhoid H1 facilitates the visualization and manipulation of further target tissue locations that may otherwise have been obstructed by swollen tissue. Once all of the devices 10 have been preliminarily positioned over their desired target portions of tissue, the ligation bands 18 may be fully tightened to ligate the corresponding portions of tissue. To fully tighten the ligation bands 18, the user threads the proximal end of a first one of the ligation bands 18 through a distal opening 52 in the trim tool 50 and out of a proximal end 54 thereof until the hub 22 abuts the distal end 56 of the trim tool 50. The distal opening 52 is sized to permit the ligation band 18 to pass therethrough while preventing the hub 22 from entering the trim tool 50.

As shown in FIG. 4, the trim tool 50 includes an outer housing 58 with an inner housing 60 rotatably received therein. The inner housing 60 includes a corresponding opening 62 which, in an initial configuration, is aligned with the distal opening 52 in the outer housing 58 so that the ligation band 18 may be fed through the trim tool 50. Edges of the distal opening 52 and the opening 62 are sharpened so that, after the ligation band 18 has been fed through the trim tool 50, the user may cut the ligation band at the openings 52, 62 by rotating the outer housing 58 over the inner housing 60 to draw the cutting edges of the openings 52, 62 laterally through the ligation band 18. That is, when the trim tool 50 is positioned with its distal end 56 abutting the hub 22, the outer housing 58 is rotated while maintaining tension on the ligation band 18 to rotate the openings 52, 62 relative to one another severing the ligation band immediately proximal of the hub 22. This process of tightening and trimming is then repeated for all additional ligation bands 18 that have been positioned as described above.

In use, the ligation band 18 of a device 10 is threaded through a trim tool 50 which is pushed distally over the ligation band 18 until the distal end 56 of the trim tool 50 abuts the proximal end of the housing 12. This assembly is then inserted through the working channel of an anoscope and the anoscope is advanced through the anus until a target portion of tissue is identified (e.g., visually using the optics of the anoscope). In this case, the hemorrhoid H1 is located and the hemorrhoid H1 is drawn proximally through the loop of the ligation band 18 (e.g., using a grasper or suction provided via the anoscope as would be understood by those skilled in the art).

When the ligation band 18 has been advanced over the hemorrhoid H1 to the position over which it is desired to eventually be tightened to ligate the tissue, the user draws the proximal end 20 of the ligation band 18 (which remains accessible outside the body through the proximal end of the working channel of the anoscope) while maintaining a distally directed force on the trim tool 50 (which also remains accessible outside the body) to pull the proximal portion of the ligation band 18 through the hub 22 to preliminarily tighten the ligation band 18 around the hemorrhoid H1 to a first desired level.

If the device 10 includes a hub 22 as described above, that is movable between a first configuration in which the ligation band 18 can be only tightened and a second configuration in which the ligation band 18 can be loosened after tightening, and the user may, if he/she wants, reposition the device 10. If the user decides to reposition the device 10, the user actuates the actuation switch 38 (e.g., by pulling a pull wire, etc.) to move the hub 22 into the second configuration. The user then pushes the proximal end 20 of the ligation band 18 distally through the hub 22 to loosen the loop of the ligation band 18 and moves the device 10 to the current desired position. When the device 10 is in the new desired position, the user again moves the hub 22 to the first configuration (e.g., by using a second pull wire or by releasing the first pull wire) and again preliminarily tightens the ligation band 18 to the desired level around the hemorrhoid H1 (or any other desired location) as described above.

That is, the physician tightens the ligation band 18 around the hemorrhoid H1 to a level sufficient to maintain the ligation band 18 in the desired position to block blood flow to the tissue but without constricting the tissue to an extent that would generate the swelling associated with ligation. As described above, the user may determine sufficient tightness of the ligation band 18 by direct visualization of the hemorrhoid through the anoscope or by a tactile change in the force required to pull the proximal end 20 of the ligation band 18 (i.e., increased resistance, indicating the ligation band 18 has tightened around the hemorrhoid). The physician then pulls the housing 12 proximally off of the ligation band 18, withdraws the housing 12 along with the trim tool 50 from the anoscope and removes both of these items from the body and from the working channel of the anoscope.

Although in the above embodiment the housing 12 is connected to the trim tool 50, the user can selectively remove the housing from the trim tool. The process is then repeated by assembling another device 10 onto the trim tool 50 and inserting this new combination through the working channel of the anoscope. The second device 10 is then placed over a second target portion of tissue (e.g., hemorrhoid H2) and preliminarily tightened in the same manner described above. When each targeted portion of tissue have had a corresponding device 10 preliminarily tightened over it in this manner, the physician may complete the procedure by tightening the devices 10 completely to ligate the tissue and removing the anoscope.

To do this, the physician threads the proximal portion of a first one of the ligation bands 18 through the openings 52, 62 of the trim tool 50 and slides the trim tool 50 distally over the ligation band 18 until the distal end 56 of the trim tool 50 abuts the hub 22. The physician then pushes the trim tool 50 distally while drawing the ligation band 18 proximally through the hub 22 to tighten the ligation band 18 to a level sufficient to strangle the encircled tissue (i.e., to ligate the tissue). When this level of tightness has been achieved, the physician abuts the distal end 56 of the trim tool 50 against the hub 22 of this tightened ligation band 18 and rotates the outer housing 58 relative to the inner housing 60 as described above to cut the ligation band immediately proximal to the hub 22. This process is repeated until all of the applied ligation bands 18 have been tightened and trimmed in this manner.

FIGS. 10-12B show a device 100 for treating hemorrhoids according to a second embodiment. The device 100 operates in a manner similar to the device 10 and allows a user to partially tighten a ligation band 118 around a target portion of tissue so that the ligation band 118 maintains its position without causing the swelling associated with the complete ligating of hemorrhoids. The device 100 includes a housing 112 similar to the housing 12 in that it is substantially Y shaped with a single proximal lumen 114 branching into first and second distal lumens 116 and 116' respectively.

The ligation band 118 extends from a proximal end (not shown) into the lumen 114 to a hub (not shown but which may be constructed in the same manner as the hub 22 or alternatives described above). The ligation band 118 extends through the hub to pass out of the lumen 116 and enter the lumen 116'. The ligation band 118 passes through the lumen 116' to re-enter the hub to which, in this embodiment, a distal end (not shown) of the ligation band 118 is immovably coupled. Those skilled in the art will understand that any of the alternatives discussed above for the interaction of the hub 22 with the ligation band may be employed in any of the described embodiments. Furthermore, other methods/structures for fixing the ligation band (e.g., crimps described below) may also be used in conjunction with any embodiment as desired.

Branches 120, 120' of the housing 112 may, for example, be biased toward a closed position in which the distal ends of the branches 120, 120' come together so that the lumens 116 and 116' are open to one another and form a complete (or nearly complete loop). The device 100 may be applied in a manner substantially similar to that described above in regard to the device 10. For example, the device 100 may be assembled with a trim tool 50 and inserted to a target location via an anoscope. As the device 10 is moved distally out of the working channel of the anoscope, the branches 120, 120' may be moved apart from one another into a tissue receiving configuration as shown in FIG. 10.

As shown in FIGS. 13-15, the device 100 of this embodiment includes pull wires 122, 122' coupled to the distal ends 124, 124' of the branches 120, 120', respectively. The branches 120, 120' extend from proximal ends 125, 125' to distal ends 124, 124'. The branches 120, 120' may contain proximal portions 121, 121' and distal portions 123, 123'. The proximal portions 121, 121' extend from proximal ends 125, 125' of the branches 120, 120' to distal openings 127, 127' and the distal portions 123, 123' extend from the distal openings 127, 127' to the distal ends 124, 124' of the branches 120, 120'. The distal portions 123, 123' are sized and shaped to slide proximally into the proximal portions 121, 121' of the branches 120, 120'. Thus, a diameter of each of the distal portions 123, 123' will be less than a diameter of each of the distal openings 127, 127'. Accordingly, the branches 120, 120' may be a rigid material (e.g., metal, hard polymers, PEEK, PC, etc.).

In this embodiment, the branches 120, 120' extend from the proximal ends 125, 125' to the distal ends 124, 124'. The branches 120, 120' may contain proximal portions 121, 121' and distal portions 123, 123'. The proximal portions 121, 121' extend from proximal ends 125, 125' of the branches 120, 120' to distal openings 127, 127' and the distal portions 123, 123' extend from the distal openings 127, 127' to the distal ends 124, 124' of the branches 120, 120'. The distal portions 123, 123' are sized and shaped to slide proximally into the proximal portions 121, 121' of the branches 120, 120'. Thus, a diameter of each of the distal portions 123, 123' will be less than a diameter of each of the distal openings 127, 127'. Accordingly, the branches 120, 120' may be a rigid material (e.g., metal, hard polymers, PEEK, PC, etc.).

Thus, when the device 100 is advanced distally out of the anoscope, the user may move the device 100 to the open, tissue receiving configuration by pulling the pull wires 122, 122' proximally. In the exemplary embodiment, when the pull wires 122, 122' are pulled proximally, the distal portions 123, 123' slide proximally into the proximal portions 121, 121' to move the branches 120, 102' into the tissue receiving configuration as shown in FIG. 10.

The device 100 may then be advanced until a target portion of tissue (e.g., hemorrhoid H3) is received between the branches 120, 120'. The user then releases the pull wires 122, 122' and allows the branches 120, 120' to revert to the closed tissue capture configuration under their natural bias as shown in FIG. 12A. When the distal ends 124, 124' meet one another with the hemorrhoid H3 received between the branches 120, 120', the lumens 116, 116' are open to one another. The user, then threads a ligation band 118 through the lumen 114 into the lumen 116 and into the lumen 116' so that it passes back into the lumen 114. The ligation band 118 may then be attached to a hub (like the hub 22) and tightened to a preliminary level in the same manner described above.

The device 100 also includes a slit 126 extending through the radially inner, distal surfaces of the branches 120, 120' so that, after the ligation band 118 has been preliminarily tightened around the hemorrhoid H3, the user may pull the housing 112 proximally off of the ligation band 118 and withdraw the housing 112 and the trim tool 50 from the body in the same manner described above. This may be done for all of the hemorrhoids to be treated. Then, when ligation bands 118 have been placed as desired on all of the hemorrhoids to be treated, the user may fully tighten the ligation bands 118 and trim them using the trim tool 50 in the same manner described above.

As shown in FIGS. 16A, 16B, and 16C, a device 200 according to a third embodiment operates substantially similarly to the device 10 except that the device 200 includes branches 220, 220' designed to separate from a proximal housing 212 and, as the ligation band 218 is tightened around the target portion of tissue (hemorrhoid H4), collapse against the hemorrhoid H4. Proximal ends 221, 221' are releasably coupled to distal ends 213, 213' of the housing 212 via a mechanical coupling such as reduced diameter portions of the distal ends 213, 213' that are snugly received within the lumens 216, 216' of the branches 220, 220', respectively, via an ID/OD interference fit, adhesive, etc.

Alternatively, their proximal ends 221, 221' may be integrally formed with the distal ends 213, 213' with predetermined failure points generated (e.g., by perforations or other weakened portions). Specifically, the device 200 is preliminarily positioned, the ligation band 218 is passed therethrough and preliminarily tightened as described above and left in position over the target hemorrhoid. At this point, the user may pull the housing 212 proximally pulling the ligation band 218 distally out of a slit 222 that extends across the distal end of the housing 212 and the housing 212 is removed from the body. As the branches 220, 220' do not include such a slit, as the proximal housing 212 is pulled off of the ligation band 218, the branches 220, 220' remain over the ligation band 218 around the hemorrhoid H4.

The user may then pull the proximal end of the ligation band 218 proximally through the hub to tighten the ligation band 218 to an initial level. The initial level refers to the ligation band 218 being tightened around the hemorrhoid H4 to remain on the hemorrhoid H4 without fully constricting blood flow to the hemorrhoid H4. When a device 200 has been preliminarily positioned over every one of the target hemorrhoids as described above, the user fully tightens each ligation band 218 by threading a trim tool 50 over the ligation band 218 in the same manner described above in regard to the device 100 and the process is repeated for all of the targeted hemorrhoids.

In addition, the device 200 may be used in conjunction with a banding agent 240 slid through a lumen 214 of the device 200 so that each of the prongs 242, 242' of the banding agent 240 enters a corresponding one of the lumens 216, 216'. The banding agent 240, which may also pass through the slit 222, is formed so that it will laterally compress the branches 220, 220' against one another to apply further pressure to the ligated tissue. The banding agent 240 may be formed to assume a preselected shape to better compress the target tissue. For example, the banding agent 240 may be formed of heat-treated Nitinol or may include a shape memory center section 244 coming to a point 246 to enhance the compression provided as would be understood by those skilled in the art.

As would be understood by those skilled in the art, a banding agent 240 formed of Nitinol may be configured so that, a body heat is absorbed by the banding agent 240, and thus the banding agent 240 changes to a previously memorized shape to constrict the hemorrhoid. Alternatively, the banding agent 240 (if inert) may be threaded through the lumens 216, 216' in the same manner as the ligation band 218 (without the use of a ligation band 218) and then the ends of the prongs 242, 242' may be coupled to one another and tightened using a crimp as will be described in more detail below to pinch the branches 220, 220' together.

As shown in FIGS. 17-19, a device 300 according to a fourth embodiment operates substantially like the device 100 except that the device 300 includes no pull wire to open the branches 320, 320'. The branches 320, 320' of the device

300 are biased toward the tissue capture configuration in which the distal ends 324, 324' are adjacent to one another so that lumens 316, 316' in the branches 320, 320' are open to one another. The device 300 is advanced out of an anoscope in the same manner described above in regard to the device 100 and advanced distally until the distal ends 324, 324' of the branches 320, 320' contact the target tissue (e.g., hemorrhoid H5) that projects outward from the surrounding tissue. As the device 300 is urged against the hemorrhoid H5, the resistance of the tissue pushes proximally against the branches 320, 320' until the distal ends 324, 324' flex radially inward with the branches 320, 320' bending away from one another as shown in FIG. 18.

Eventually, the branches 320, 320' separate and pass around the hemorrhoid H5 until, as they extend distally beyond the hemorrhoid H5, they move toward one another under their natural bias. When the branches 320, 320' meet in the tissue capture configuration, a ligation band may be fed therethrough and preliminarily positioned and partially tightened in the same manner described above in regard to the device 100. When all of the hemorrhoids targeted in the procedure have had device 300 preliminarily placed thereon and partially tightened, the user fully tightens and trims the ligation bands for these devices 300 in the same manner described above in regard to the device 100.

As shown in FIGS. 20A-20C, a device 400 according to a fifth embodiment operates substantially similarly to the device 100 except that, instead of a flexible housing such as the housing 112 of the device 100, the device 400 includes branches 420, 420' that are pivotally coupled to the housing 412 at pivot joints 413, 413'. The branches 420, 420' are biased toward a closed, tissue capture configuration in which distal ends 424, 424' of the branches 420, 420' meet with lumens 416, 416' open to one another, positioned around a target portion of tissue (e.g., hemorrhoid H6).

The branches 420, 420' may be biased toward the closed, tissue capture configuration via, for example, torsion springs 415, 415' urging the branches 420, 420' to rotate toward one another. Pull wires 422, 422' coupled to the branches 420, 420', respectively, may then be pulled proximally to move the branches 420, 420' away from one another to the open tissue receiving configuration in the same manner described above in regard to the device 100. Radially inner surfaces 423, 423' and a distal surface 425 of the housing 412 include a slit through which a ligation band 418 may be pulled to release the device 400 from the ligation band in the same manner described above in regard to the device 100. In all other respects, the device 400 operates in substantially the same manner as the device 100.

As shown in FIGS. 21A, 21B, 22A, and 22B, a device 500 according to a sixth embodiment operates in substantially the same manner as described above for the device 100 except that the device 500, instead of having a slit like the slit 126 through which the ligation band 518 passes to free the housing 512 from the ligation band 518, the housing of the device 500 is formed of two Y-shaped sections 513, 513'. The device 500 is positioned around the hemorrhoid H7 in the same manner described for the device 100. However, when the user desires to preliminarily tighten the ligation band 518 around the hemorrhoid H7, the user first operates an actuator such as a pull wire (not shown) coupled to the Y-shaped section 513' to rotate the section 513' away from the section 513 about the pivot 515. This permits the user to preliminarily tighten the ligation band 518 in the same manner described above for the device 100 and remove the housing 512 from the body by sliding the housing 512 proximally over the ligation band 518 with the loop of the ligation band 518 passing out of the gap between the sections 513, 513'. The operation of the device 500 is otherwise substantially similar to that of the device 100.

Finally, it is noted that, in place of the hub and ratchet mechanisms described above, other devices/methods may be used to hold the ligation bands and/or banding agents in place so that they apply the desired tension to the tissue (first in the preliminary fixation step and then the higher compression of full ligation). One example of a suitable means of locking a ligation band and/or banding agent as desired is a crimp that may be crushed over the two strands of the ligation band or the prongs of the banding agent after the desired tissue compression has been achieved. As would be understood by those skilled in the art, the crimp may be formed so that, when partially crushed, it would hold the ligation band at a first tension while still permitting the ligation band to be pulled further through the crimp at a later time to increase the tension as desired.

Those skilled in the art will understand that there are various modifications that may be made to the embodiments described without departing from the teachings of this application. For example, although the embodiments have been described in regard to the treatment of internal hemorrhoids, those skilled in the art will understand that the embodiments can be used in the treatment of benign or cancerous polyps in regions of the rectum accessible by these devices. In addition, those skilled in the art will understand that many variations of these embodiments are within the scope of this disclosure including, for example, the provision of different sizes of any of the devices to address differently sized hemorrhoids, etc.

The invention claimed is:

1. A method for ligating tissue, comprising:
   tightening a first ligating member about a first portion of target tissue to an initial level of tissue compression sufficient to maintain a desired position of the first ligating member around the first portion of target tissue without significantly cutting off blood flow to the first portion of target tissue;
   after the first ligating member has been tightened to the initial level of tissue compression, tightening a second ligating member about a second portion of target tissue to the initial level of tissue compression; and
   after the second ligating member has been tightened to the initial level of tissue compression, tightening the first ligating member about the first portion of target tissue to a final level of tissue compression sufficient to cut off blood flow to the first portion of target tissue and tightening the second ligating member about the second portion of target tissue to the final level of tissue compression.

2. The method of claim 1, wherein a trimming device contains an outer housing with a sharpened outer opening and an inner housing rotatably received therein with a sharpened inner opening, the method further comprising, aligning the outer opening and inner opening, inserting a proximal portion of the first ligating member through the outer opening and inner opening, rotating the outer housing relative to the inner housing to remove the proximal portion from the first ligating member, and after removing the proximal portion of the first ligating member, re-aligning the outer opening with the inner opening, inserting a proximal portion of the second ligating member through the outer opening and inner opening, and rotating the outer housing relative to the inner housing to remove the proximal portion from the second ligating member.

3. The method of claim 1, further comprising:

tightening to the initial level the first ligating member around the first portion of target tissue by drawing a proximal portion of the first ligating member through a hub within an applicator, the first ligating member passing into a proximal lumen of the applicator through the hub and into a first distal lumen of the applicator, looping out of a distal end of the first distal lumen of the applicator and entering a distal end of a second distal lumen of the applicator, wherein a user places the first portion of target tissue within a loop of the first ligating member extending between the distal ends of the first and second distal lumens of the applicator.

4. The method of claim 3, further comprising:

after tightening the first ligation member to the initial level, tightening to the initial level the second ligating member around the second portion of target tissue by drawing a proximal portion of the second ligating member through the hub within the applicator, the second ligating member passing into the proximal lumen of the applicator through the hub and into the first distal lumen of the applicator, looping out of the distal end of the first distal lumen of the applicator and entering the distal end of the second distal lumen of the applicator, wherein the user places the second portion of target tissue within the loop of the second ligating member extending between the distal ends of the first and second distal lumens of the applicator.

5. The method of claim 4, further comprising:

after tightening the first and second ligation members to the initial level, tightening the first ligating member about the first portion of target tissue to the final level and tightening the second ligating member about the second portion of target tissue to the final level.

6. The method of claim 3, wherein the hub includes a ratchet mechanism and an actuation switch, the method further comprising:

moving the actuation switch into a first position in which an engagement member of the ratchet mechanism prevents a loosening of the loop of the first ligating member.

7. The method of claim 6, further comprising:

moving the actuation switch into a second position to move the engagement member of the ratchet mechanism out of engagement with the first ligating member to permit the first ligating member to move through the hub in tightening and loosening directions.

8. The method of claim 3, wherein the applicator is formed as a substantially Y shaped housing with the first and second distal lumens thereof extending through first and second branches, respectively, the first and second branches of the applicator being biased toward a tissue capture configuration in which the distal ends of the first and second distal lumens of the applicator are open to one another.

9. The method of claim 8, further comprising:

advancing the applicator to a position adjacent to the first portion of target tissue;

actuating the applicator into a tissue receiving configuration in which the first and second branches of the applicator are drawn apart;

positioning the applicator so that the first portion of target tissue is between the first and second branches of the applicator; and reverting the applicator into the tissue capture configuration in which the first and second branches of the applicator are drawn together around the first portion of target tissue.

10. The method of claim 9, further comprising loading the first ligating member into the applicator prior to advancing the applicator to the position adjacent to the first portion of target tissue.

11. The method of claim 9, wherein the applicator includes a first pull wire coupled to the first branch of the applicator and a second pull wire coupled to the second branch of the applicator.

12. The method of claim 11, wherein the applicator is actuated into the tissue receiving configuration by proximally drawing the first and second pull wires and wherein the applicator is reverted back into the tissue capture configuration by releasing the first and second pull wires.

13. The method of claim 3, wherein the applicator includes a slit on a distal surface thereof through which the first ligating member may pass after the first ligating member has been placed around the first portion of target tissue so that the applicator may be withdrawn from a body while leaving the first ligating member in place around the first portion of target tissue.

14. The method of claim 3, further comprising moving the hub into a first configuration in which the loop of the first ligating member, which extends from the hub through the first distal lumen of the applicator and back through the second distal lumen of the applicator to the hub, can only be tightened.

15. The method of claim 14, further comprising moving the hub into a second configuration in which the loop of the first ligating member can be loosened and tightened.

16. The method of claim 3, further comprising inserting the applicator through a working channel of an insertion device inserted into a living body.

* * * * *